United States Patent [19]

Bagwell

[11] 4,328,708
[45] May 11, 1982

[54] ROTARY ULTRASONIC TESTING APPARATUS

[75] Inventor: Alan D. Bagwell, Taunton, England

[73] Assignee: British Steel Corporation, England

[21] Appl. No.: 153,292

[22] Filed: May 27, 1980

[51] Int. Cl.³ .............................................. G01N 29/04
[52] U.S. Cl. ........................................ 73/622; 73/634
[58] Field of Search ................ 73/622, 625, 633, 634, 73/637, 640, 641

[56] References Cited

U.S. PATENT DOCUMENTS 3,077,768  2/1963  Allardt et al. ..................... 73/634
3,837,202  9/1974  Hetherington et al. ........ 73/641 X

*Primary Examiner*—James J. Gill
*Attorney, Agent, or Firm*—Bacon & Thomas

[57] ABSTRACT

A rotary ultrasonic testing apparatus includes an annular stator; an annular rotor mounted on the stator for rotation about a workpiece to be tested as it is moved through the stator and rotor; and an ultrasonic probe assembly mounted for rotation with the rotor, said probe assembly comprising a cranked arm pivotally mounted at the crank thereof upon a bearing pin having an axis parallel to the axis of the rotor, the cranked arm carrying towards one end an adjustable counterweight and at the other end an ultrasonic probe block and guide shoe for facing to the surface of the workpiece, said bearing pin being adjustable in position relative to the rotor axis, spring means for limiting movement of the arm about the bearing pin, and water supply means connected to the probe pad.

7 Claims, 2 Drawing Figures

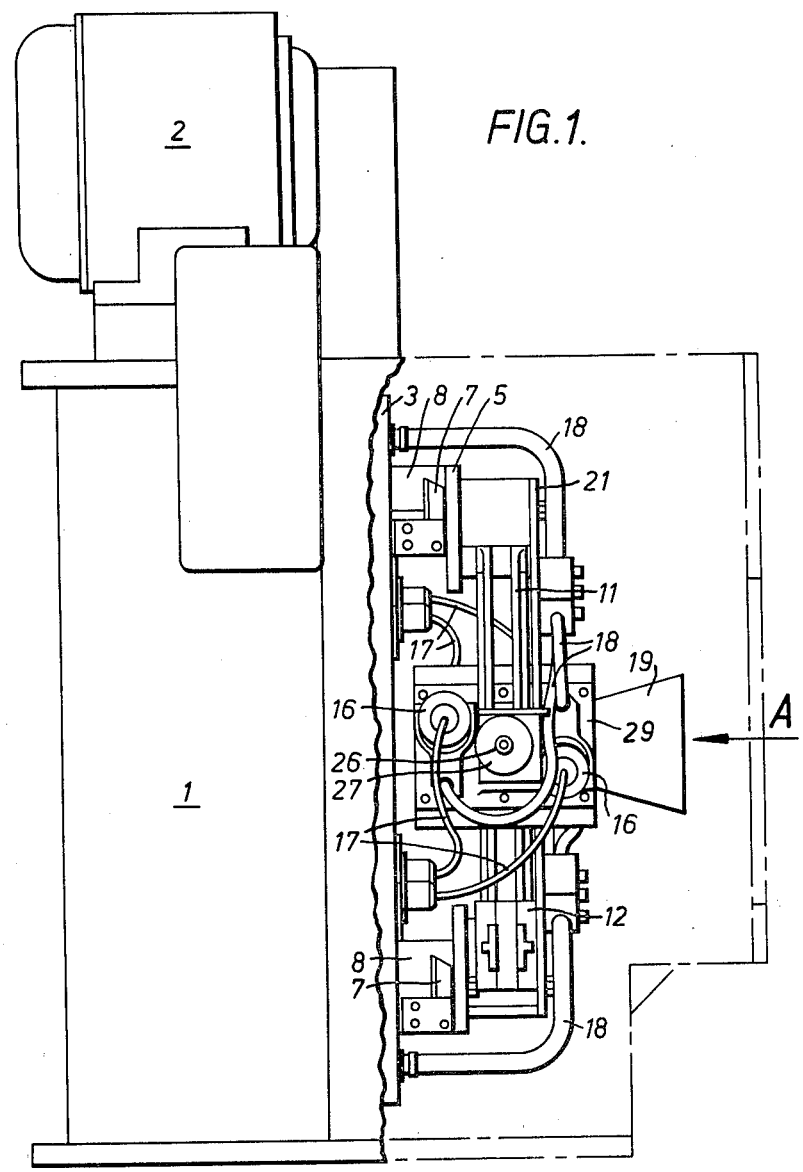

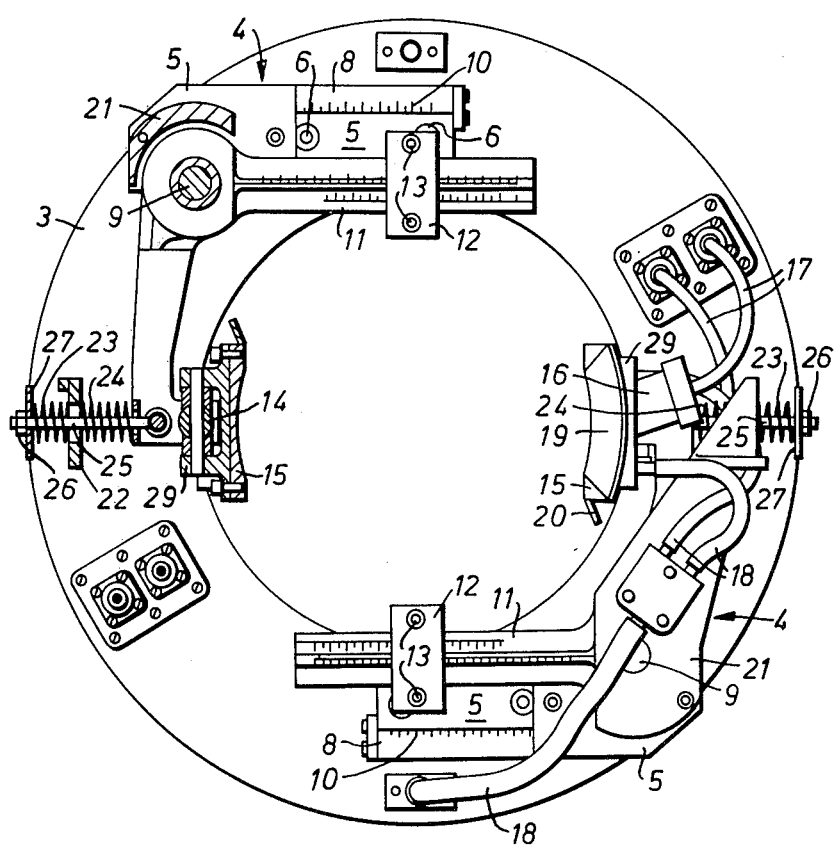

ROTARY ULTRASONIC TESTING APPARATUS

This invention relates to rotary ultrasonic testing apparatus for the kind used to test elongate articles of generally uniform cross-section, such as steel tubes or bars for example, for flaws and dimensional accuracy by rotating an ultrasonic probe assembly in a close pitched spiral about the articles, whilst acoustically coupling the probe assembly to the articles by means of a liquid such as water.

It is an object of the present invention to provide rotary ultrasonic testing apparatus of this kind in which the probe assembly can be applied accurately and rapidly to a range of sizes.

According to the invention there is provided rotary ultrasonic testing apparatus including an annular stator; an annular rotor mounted on the stator for rotation about a workpiece to be tested as it is moved through the stator and rotor; and an ultrasonic probe assembly mounted for rotation with the rotor; wherein said probe assembly comprises a cranked arm pivotally mounted at the crank thereof upon a bearing pin having an axis parallel to the axis of the rotor, the cranked arm carries towards one end an adjustable counterweight and at the other end an ultrasonic probe block and guide shoe for facing to the surface of the workpiece, said bearing pin being adjustable in position relative to the rotor axis, spring means for limiting movement of the arm about the pivot pin, and water supply means connected to the probe pad.

In operation rotation of the rotor causes the counterweight to swing the cranked arm about the pivot pin such that the probe pad is forced into contact with the workpiece as it is passed through the apparatus. The adjustability of the counterweight and the pivot pin enables the apparatus to accomodate a plurality of sizes of workpiece.

In order that the invention may be more readily understood one embodiment thereof will now be described by way of example with reference to the accompanying drawings in which:

FIG. 1 is a partially sectioned side elevation of rotary ultrasonic testing apparatus according to the invention; and FIG. 2 is an elevation in the direction of arrow "A" of FIG. 1.

Referring to the drawings, it is to be seen that the apparatus is mounted in a housing 1 and comprises an annular stator (not shown) of known kind disposed behind the left hand side of the housing 1 in FIG. 1.

A rotor 3 is mounted for rotation in known manner on the stator, the rotor being chain or belt driven from a motor 2.

Slip rings (not shown) of known kind are used for supplying power to the probes described hereinafter.

Elongate workpieces (such as steel tubes) are adapted to be fed into the apparatus in the direction of the arrow marked "A" in FIG. 1.

The face of the rotor 3 directed towards incoming workpieces carries two ultrasonic probe assemblies 4 as hereinafter described.

Each assembly 4 comprises a support block 5 carried by screws 6 on a wedge bar 7 moveable along a groove in a support rail 8 permanently secured to the face of the rotor 3. The support block 5 carries a bearing pin 9, and by adjustment of the block 5 along the rail 8 the position of the pin 9 relative to the axis of the rotor can be varied. A suitable scale 10 is provided along the rail 8.

Pivotally mounted on pin 9 is a cranked arm 11. One side of the arm 11 carries a counterweight 12, adjustable along the arm by means of screws 13. A suitable scale is again provided on arm 11.

The cranked arm 11 carries at its other end, on a ball joint 14, a probe block 29, the block carrying two ultrasonic probes 16. Attached to the probe block 29 is a guide shoe 15 having leading and transverse angle faces 19 and 20 to assist in correct engagement of the guide shoe 15 on incoming workpieces. Leads 17 provide power to the probes and hoses 18 supply water for acoustic coupling purposes.

A cantilever arm 21 is fixedly secured to the support block 5 adjacent to the pivot pin 9. At its end remote from the pin 9 the cantilever arm 21 carries a spring support plate 22 which separates and engages two springs 23 and 24 mounted on a rod 25 attached at one end to the arm 11. The free end of the rod 25 is threaded and carries a nut 26 and washer 27 which bears upon the spring 23. Nut 26 controls the tension in springs 23 and 24.

In operation of the apparatus, the two probe assemblies 4 are adjusted by positioning support blocks 5 along rails 8 such that the pivot pins 9 are correctly spaced from the axis of the rotor to provide correct positioning of the guide shoes 15 on the size of the workpiece to be tested.

A rotor is then turned (clockwise as viewed in FIG. 2) so that the counterweights pivot the arms 11 about pins 9, thereby moving probe pads 15 inwards towards the axis of the rotor 3 until restrained by spring 23.

A tube to be tested is then fed into the apparatus engaging firstly on leading guide shoes 19 of pads 15, and then engaging pads 15 themselves. The probes 16 are acoustically coupled to the incoming tube by flowing water from hoses 18 and ultrasonic testing can commence immediately. The probes transcribe a close pitched spiral around the periphery of the tube as it passes through the apparatus.

In operation, movement outwards or inwards, of the probe block 29 from an optimum position is restrained and limited by springs 23 and 24 thereby reducing bounce of the block 29 and also reducing wear on the guide shoe 15.

As will be appreciated the apparatus hereinbefore described is compact and efficient in operation, and capable of considerable adjustment to accomodate the requirements of different workpieces.

It is particularly advantageous on rough hot finished surfaces.

I claim:

1. A rotary ultrasonic testing apparatus including an annular stator; an annular rotor mounted on the stator for rotation about a workpiece to be tested as it is moved through the stator and rotor; and an ultrasonic probe assembly mounted for rotation with the rotor, said probe assembly comprising a cranked arm pivotally mounted at the crank thereof upon a bearing pin having an axis parallel to the axis of the rotor, the cranked arm carrying towards one end an adjustable counterweight and at the other end an ultrasonic probe block and guide shoe for facing to the surface of the workpiece, said bearing pin being adjustable in position relative to the rotor axis, spring means for limiting movement of the arm about the bearing pin, and water supply means connected to the probe pad.

2. Testing apparatus as claimed in claim 1 wherein said arm is cranked by an angle of the order of one right angle.

3. Testing apparatus as claimed in claim 1 or 2 wherein the general plane of the cranked arm is at right angles to the axis of the bearing pin.

4. Testing apparatus as claimed in claim 1 or 2 wherein the arm in cranked such that the end thereof carrying the adjustable counterweight is turned back from the bearing pin towards the path of the workpiece.

5. Testing apparatus as claimed in claim 1 wherein the spring means is mounted adjacent the ultrasonic probe block and is adapted to limit movement of the block both towards and away from the path of the workpiece.

6. Testing apparatus as claimed in claim 5 wherein the spring means is mounted on a member movable with adjustments in position of the bearing pin.

7. Testing apparatus as claimed in claim 1 wherein adjustment of the bearing pin is provided by mounting the pin on a member movably mounted on a slide carried by the rotor.

* * * * *